United States Patent
Berggren et al.

(10) Patent No.: US 8,323,167 B2
(45) Date of Patent: Dec. 4, 2012

(54) METHOD FOR MANUFACTURING A PANTS-TYPE DIAPER

(75) Inventors: Ulf Berggren, Göteborg (SE); Lennart Nilsson, Skärhamn (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 13/377,909

(22) PCT Filed: Jun. 26, 2009

(86) PCT No.: PCT/SE2009/050822
§ 371 (c)(1),
(2), (4) Date: Dec. 13, 2011

(87) PCT Pub. No.: WO2010/151195
PCT Pub. Date: Dec. 29, 2010

(65) Prior Publication Data
US 2012/0088646 A1     Apr. 12, 2012

(51) Int. Cl.
*B31B 1/00*     (2006.01)
(52) U.S. Cl. ........................................ 493/393; 493/397
(58) Field of Classification Search .................. 493/393, 493/394, 397
See application file for complete search history.

(56) References Cited

U.S. PATENT DOCUMENTS

| 4,720,415 | A | * | 1/1988 | Vander Wielen et al. ...... 428/152 |
| 4,789,699 | A | * | 12/1988 | Kieffer et al. ................. 524/271 |
| 5,226,992 | A | | 7/1993 | Morman |
| 2003/0062121 | A1 | | 4/2003 | Franklin et al. |
| 2004/0030318 | A1 | | 2/2004 | Karlsson et al. |

FOREIGN PATENT DOCUMENTS

| EP | 0 646 062 | 8/1996 |
| EP | 1 035 818 | 4/2002 |
| EP | 1 764 069 | 3/2007 |
| WO | 98/29251 | 7/1998 |
| WO | 03/000165 | 1/2003 |
| WO | 03/047488 | 6/2003 |
| WO | 2004/004620 | 1/2004 |

* cited by examiner

*Primary Examiner* — Sameh H. Tawfik
(74) *Attorney, Agent, or Firm* — Drinker Biddle Reath LLP

(57) ABSTRACT

A method for facilitating the alignment of first and second side panel portions of a pants-type diaper whilst feeding a pants-type diaper precursor in a machine direction through processing apparatus. The pants-type diaper precursor includes a leading edge region, a trailing edge region and first and second side edge regions, each of the first and second side edge regions having a first side panel portion at the leading edge region and a second side panel portion at the trailing edge region. The method includes applying elastic elements under tension to a flat continuous web having a predetermined width in the cross-machine direction, the web forming either the backsheet or the topsheet of the pants-type diaper. The elastic element in the trailing edge region is adapted to generate a greater gathering force than the elastic element in the leading edge region such that the first and second panels are better aligned when brought into overlapping relationship.

16 Claims, 5 Drawing Sheets

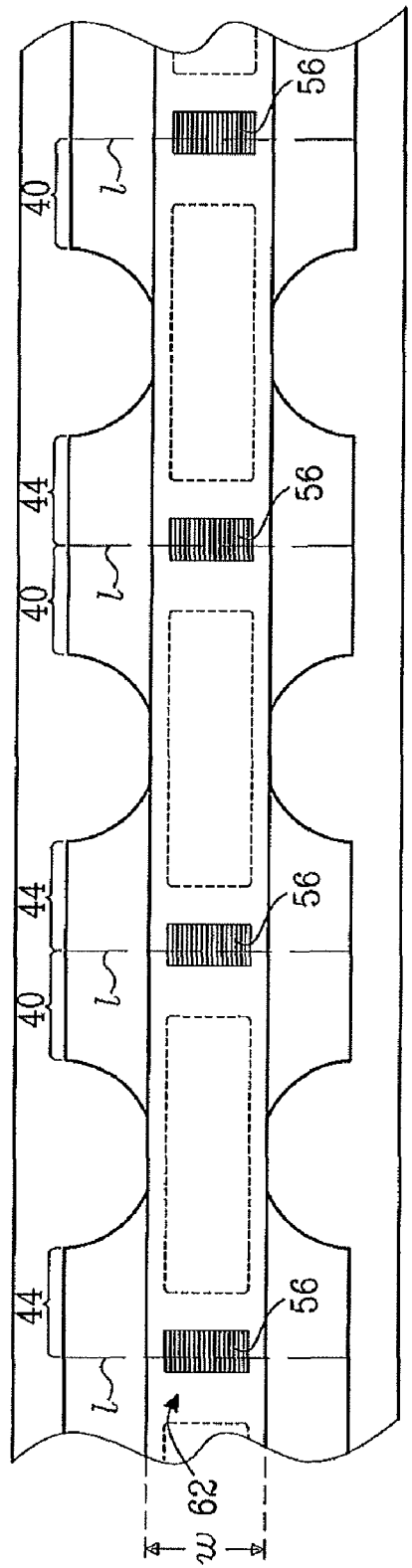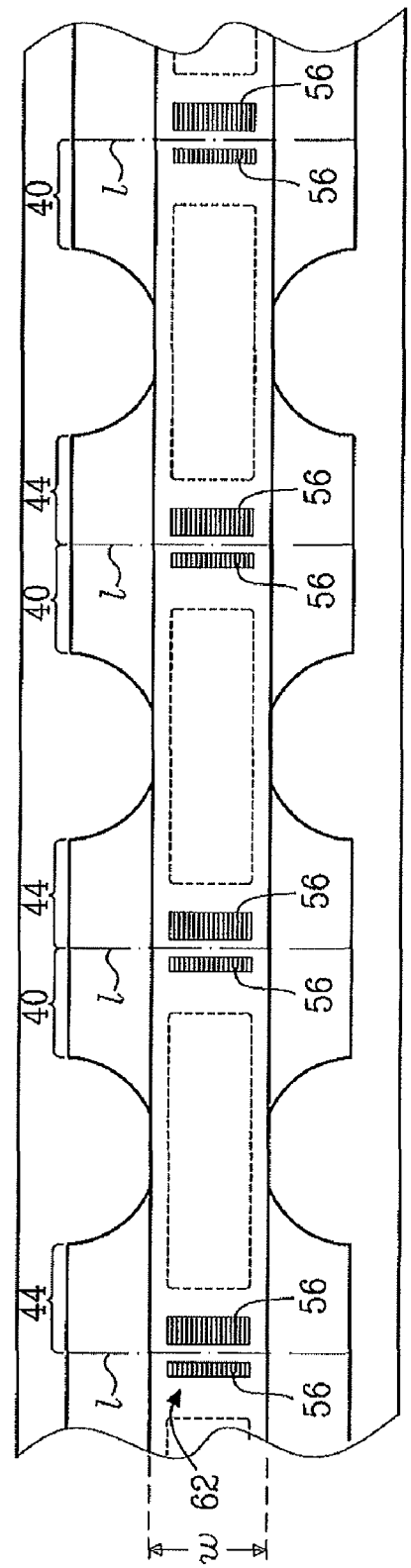

METHOD FOR MANUFACTURING A PANTS-TYPE DIAPER

CROSS-REFERENCE TO PRIOR APPLICATION

This application is a §371 National Stage Application of PCT International Application No. PCT/SE2009/050822 filed Jun. 26, 2009, which is incorporated herein in its entirety.

TECHNICAL FIELD

The present disclosure relates to a method of manufacturing a pants-type diaper and more particularly to a method for facilitating the alignment of first and second side panel portions of a pants-type diaper during manufacture.

BACKGROUND

A typical pants-type diaper has a front panel region which is intended to lie over the abdomen of a wearer, a rear panel region which is intended to lie over the buttocks of a wearer and a crotch region between the front and rear panel regions. Side panels, normally of an elasticized material, join the front and rear panels to form a continuous waist opening. Each side panel is made up of a first side panel portion adjacent the front panel and a second side panel portion adjacent the rear panel. During manufacture, the front and rear panels of a pants-type diaper precursor are folded over each other such that the first and second side panel portions overlap. Side panel seams are then formed along the laterally outermost margins of the first and second side panel portions to thereby create a closed pants-type diaper.

When forming the side panel seams, it is important that the first and second side panel portions are correctly aligned, otherwise the seams will be misplaced. Such misplacement may result in a weak product which is liable to fail in use or in an ill-fitting garment. In either case, misplaced seams are unattractive and compromise the quality of the product.

During manufacture of pants-type diapers in which the longitudinal direction of the diapers corresponds to the machine direction, the folding over of the front and rear panels means that the panel which initially is first in the machine direction has to be released from the conveyor arrangement carrying the diaper and folded over the subsequent panel which is still retained on the conveyor arrangement. As the folding is taking place, the diaper precursor is transferred to a subsequent conveyor arrangement along which the side panel seams are formed. This implies that the panel which initially is first in the machine direction is unsupported by the conveyor arrangement for a considerably longer period of time than the subsequent panel. This lack of support can lead to misalignment of the first and second side panel portions.

Problems with misplacement of the side panel seams are exacerbated when the front and/or rear panels are provided with waist elastic. During manufacture, the pants-type diaper precursor is initially temporarily secured to the conveyor arrangement in a substantially flat, laid-out condition. During folding and transfer, one or both of the panels of the diaper precursor are no longer retained on the conveyor arrangement, as a result of which the panels will contract in the cross-machine direction as the waist elastic gathers the material of the panels.

Misalignment of the first and second side panel portions has been addressed in the past by implementing corrective measures downstream of the folding step immediately prior to forming the side panel seams. Such corrective measures may include drawing out the first and second side panel portions by nipping the panel portions between an obliquely angled chain and the conveyor arrangement. It would be beneficial if it could be ensured that the first and second side panel portions are sufficiently accurately aligned without the need for extensive corrective measures.

SUMMARY

It is desired to provide a method of manufacturing a pants-type diaper in which the need for alignment correction of the side panel portions after folding is reduced.

This can be achieved in accordance with the present disclosure by a method for facilitating the alignment of first and second side panel portions of a pants-type diaper whilst feeding a pants-type diaper precursor in a machine direction through processing apparatus. The pants-type diaper precursor has a leading edge region, a trailing edge region and first and second side edge regions. Each of the first and second side edge regions has a first side panel portion at the leading edge region and a second side panel portion at the trailing edge region. The method includes the steps of:

a. providing a flat continuous web having a predetermined width in the cross-machine direction;
b. temporarily securing the continuous web to a first conveyor arrangement of the processing apparatus whilst substantially maintaining the predetermined width of the continuous web;
c. securing the side panel portions to the continuous web;
d. securing elastic elements under tension in the cross-machine direction to selected regions of the continuous web whilst substantially maintaining the predetermined width of the continuous web, the selected regions corresponding at least to said trailing edge region of said pants-type diaper precursor;
e. severing the continuous web whilst substantially maintaining the predetermined width of the continuous web to thereby form a plurality of the pants-type diaper precursors;
f. advancing the pants-type diaper precursor towards a folding unit at which the leading edge region is released from the first conveyor arrangement;
g. bringing the first and second side panel portions into overlapping relationship;
h. transferring the pants-type diaper precursor to a second conveyor arrangement at which the trailing edge region is temporarily secured to the second conveyor arrangement, and
i. forming seams along edge margins of the first and second side panel portions to thereby form a pants-type diaper, whereby
j. the step of securing elastic elements under tension in the cross-machine direction to selected regions of the continuous web whilst substantially maintaining the predetermined width of the continuous web is carried out so as to provide a pants-type diaper in which a force difference is present between the force necessary to cause the trailing edge region to attain the predetermined width and the force necessary to cause the leading edge region to attain the predetermined width, with the force for the trailing edge region being greater than the force for the leading edge region.

Since the leading edge region of the pants-type diaper precursor is released from the conveyor arrangement for a relatively long period of time to permit folding of the diaper precursor whilst the trailing edge region is retained on the conveyor arrangement for substantially all of this period, the fact that a force difference is present between the force necessary to cause the trailing edge region to attain the predetermined width and the force necessary to cause the leading edge region to attain the predetermined width, with the force for the trailing edge region being greater than the force for the leading edge region, means that the degree of contraction or necking of the leading edge region and the trailing edge region when they are unsupported by the conveyor arrangement will be essentially the same, even though the leading edge region is unsupported for a much longer period than the trailing edge region. As such, the first and second side panel regions will tend to arrive at the seam-forming station in correct overlapping relationship for forming the seams.

In example embodiments, the force difference is between 1.0 N and 5.0 N, preferably between 1.5 N and 4.0 N, more preferably between 2.0 N and 4.0 N.

In example embodiments, during the step of securing elastic elements under tension in the cross-machine direction to selected regions of the continuous web whilst substantially maintaining the predetermined width of the continuous web, the selected regions correspond solely to the trailing edge region of the pants-type diaper precursor.

In example embodiments, during the step of securing elastic elements under tension in the cross-machine direction to selected regions of the continuous web whilst substantially maintaining the predetermined width of the continuous web, the selected regions correspond to the trailing edge region and the leading edge region of the pants-type diaper precursor.

In example embodiments, a single elastic element applied under tension is applied to a selected region of the continuous web, the selected region corresponding to both the trailing edge region and the leading edge region of the pants-type diaper precursor.

In example embodiments, during the step of severing the continuous web the single elastic element is severed such that a greater portion of the elastic element is provided in the trailing edge region of a pants-type diaper precursor than in the leading edge region of an adjacent pants-type diaper precursor.

In example embodiments, the pants-type diaper precursor has an absorbent structure sandwiched between a first web and a second web, one of the first and second webs being constituted by a section of the continuous web, the first web being intended to be worn against a wearer's skin and the second web being intended to be worn against a wearer's clothing, whereby during the step of advancing the pants-type diaper precursor towards a folding unit, the first web faces the first conveyor arrangement immediately prior to folding.

In example embodiments, the pants-type diaper precursor has an absorbent structure sandwiched between a first web and a second web, one of the first and second webs being constituted by a section of the continuous web, the first web being intended to be worn against a wearer's skin and the second web being intended to be worn against a wearer's clothing, whereby during the step of advancing the pants-type diaper precursor towards a folding unit, the second web faces the first conveyor arrangement immediately prior to folding.

The first conveyor arrangement may include at least one revolving drum.

In example embodiments, during the step of transferring the pants-type diaper precursor to a second conveyor arrangement at which the trailing edge region is temporarily secured to the second conveyor arrangement, the second web of the pants-type diaper precursor is caused to face the second conveyor arrangement.

The pants-type diaper precursor may be temporarily secured to the first and second conveyor arrangements at least by suction.

In example embodiments, the step of forming seams along edge margins of the first and second side panel portions is performed using ultrasonic welding equipment, in particular rotary ultrasonic welding equipment.

In example embodiments, between the steps of bringing the first and second side panel portions into overlapping relationship, and forming seams along edge margins of the first and second side panel portions, the method further includes the step of causing air to be blown onto the first and second side panel portions to assist in maintaining alignment thereof.

In example embodiments, the elastic elements are constituted by a ribbon of elastomeric material, such as natural rubber, synthetic rubber or a thermoplastic elastomeric polymer, a stretch-bonded laminate, a neck-bonded laminate, or an elastic nonwoven such as meltblown or spunblown urethane. The elastic elements may be constituted by a three-layered laminate of PP-SBS-PP, in which PP is polypropylene and SBS is styrene/butadiene/styrene.

BRIEF DESCRIPTION OF THE DRAWINGS

The embodiments of the invention will be described in greater detail in the following by way of example only and with reference to the attached drawings in which:

FIGS. 5A and 5B are schematic views in the direction of arrow B in FIGS. 3 and 4.

DETAILED DESCRIPTION OF PREFERRED EMBODIMENTS

Figure 1:
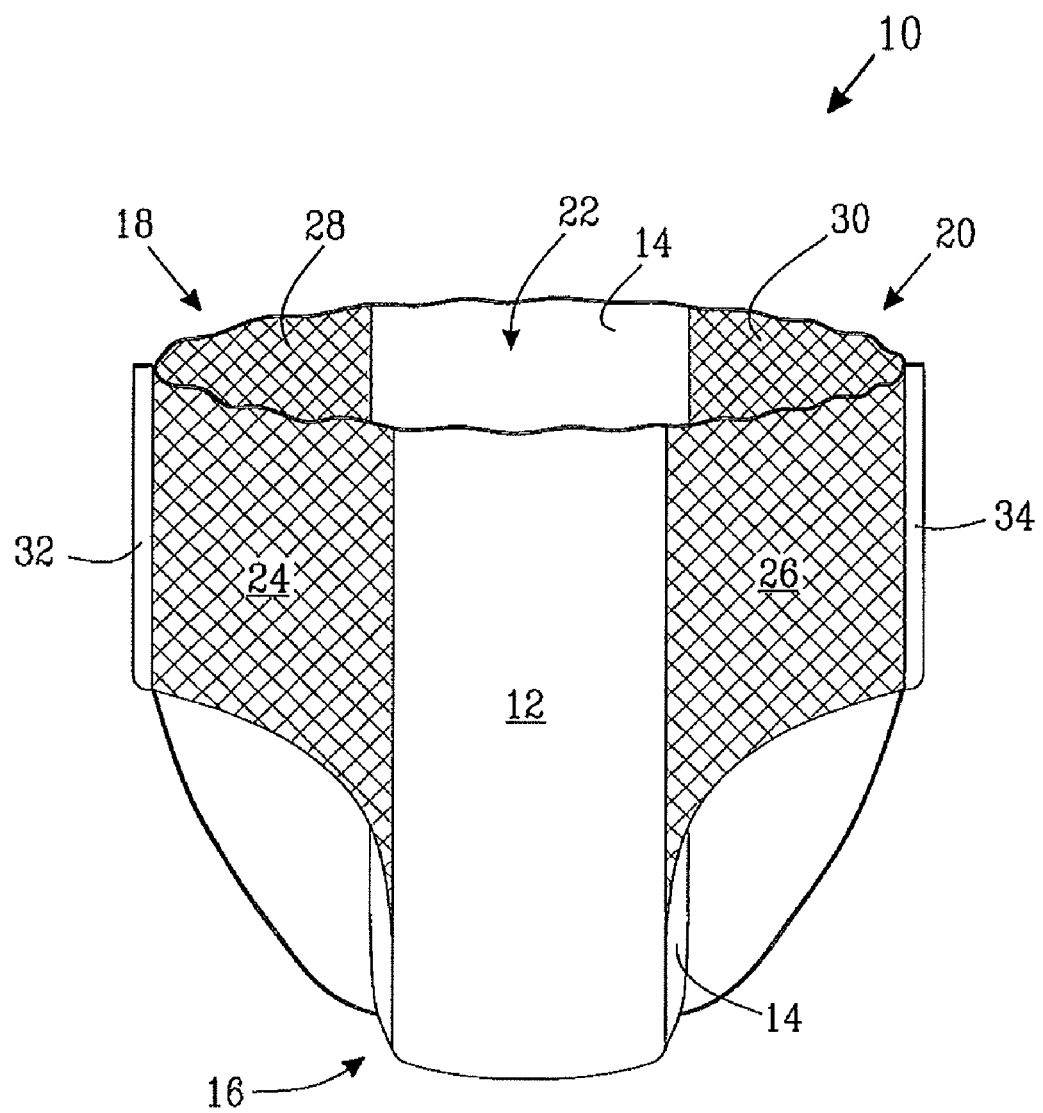
FIG. 1 is a schematic perspective view of a pants-type diaper which may be manufactured by the method in accordance with an embodiment of the present invention.

In the drawings, reference number 10 generally denotes a pants-type diaper which may be manufactured using the method of an embodiment of the present invention. Such a diaper has a front panel region 12 which is intended to lie over the abdomen of a wearer, a rear panel region 14 which is intended to lie over the buttocks of a wearer and a crotch region 16 between the front and rear panel regions. Side panels, 18, 20, normally of an elasticized material, join the front and rear panel regions to form a continuous waist opening 22. Each side panel 18, 20 is made up of a first side panel portion 24, 26 adjacent the front panel 12 and a second side panel portion 28, 30 adjacent the rear panel 14. Side panel seams 32, 34 are formed along the laterally outermost margins of the first and second side panel portions 24, 28; 26, 30 to thereby create a closed pants-type diaper.

Figure 2:
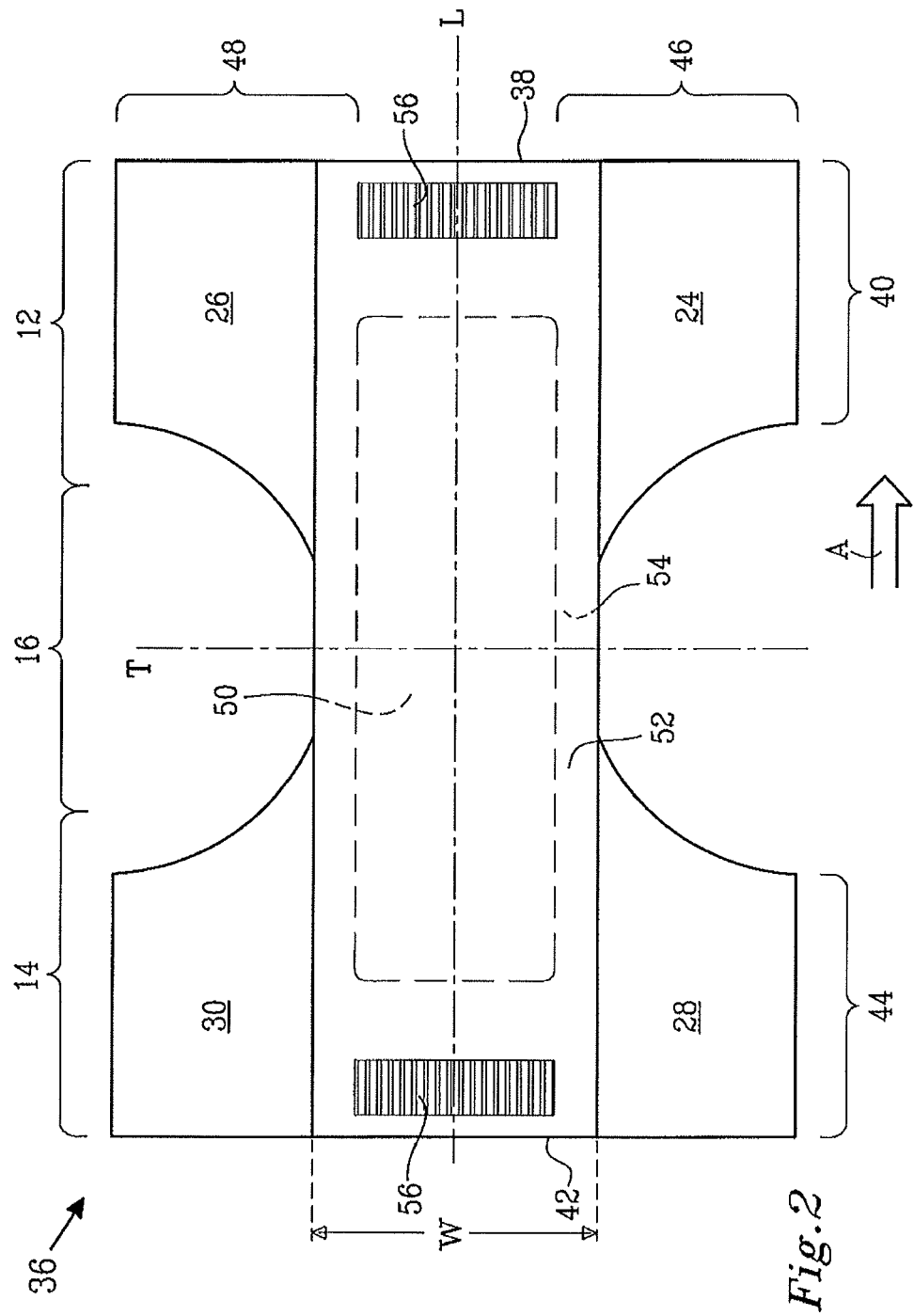
FIG. 2 is a schematic plan view of a pants-type diaper precursor suitable for use in the method of an embodiment of the present invention.

With particular reference to FIG. 2, the pants-type diaper 10 is made from a pants-type diaper precursor 36. The precursor is intended to be fed through processing apparatus in the machine direction denoted by arrow A. The portions of the precursor which correspond to the pants-type diaper of FIG. 1 are denoted by the same reference numbers. The precursor 36 extends in a longitudinal direction about a longitudinal axis L such that the precursor is essentially symmetrical about this axis. The precursor also extends in a transverse direction about a transverse axis T, with the transverse axis being half way along the longitudinal extension of the precursor. The precursor 36 has a leading edge 38 partially delimiting a leading edge region 40 which extends towards the transverse axis T. The leading edge region 40 is hereby defined as extending at least half way from the leading edge 38 to the transverse axis T. Similarly, the precursor has a trailing edge 42 partially delimiting a trailing edge region 44 which extends at least half way to the transverse axis T. The precursor 36 further includes first and second side edge regions 46, 48. The first side edge region 46 includes the first side panel portion 24 at the leading edge region 40 and the second side panel portion 28 at the trailing edge region 44. Likewise, the second side edge region 48 includes the first side panel portion 26 at the leading edge region 40 and the second side panel portion 30 at the trailing edge region 44. In the illustrated embodiment, the precursor has an absorbent structure 50 sandwiched between a first web 52 and a second web 54. The first web 52 is intended to be worn against a wearer's skin and is usually referred to as a topsheet. The second web 54 is intended to be worn against a wearer's clothing and is usually referred to as a backsheet. For reasons of comfort and fit, the precursor may also include waistband elastic 56 in the trailing edge region 44 and, optionally, in the leading edge region 40. The waistband elastic 56 may be constituted by any conventional elastic elements, for example ribbons (including bands or strips) or threads. In particular embodiments, the elastic elements are constituted by a ribbon of elastomeric material, such as natural rubber, synthetic rubber or a thermoplastic elastomeric polymer, a stretch-bonded laminate, a neck-bonded laminate, or an elastic nonwoven such as meltblown or spunblown urethane. Purely by way of example, a suitable three-layered elastic film or ribbon can be obtained from Nordenia International AG having the product code KC-6325. This is a PP-SBS-PP laminate in which PP is polypropylene and SBS is styrene/butadiene/styrene. The elastic material has a thickness of 50 µm and can be obtained on a roll of 60 mm width. Suitable elastic elements for use in embodiments of the present invention can be obtained by cutting a 27 mm length from the roll to thereby provide an elastic element having non-tensioned dimensions of 60 mm×27 mm×50 µm.

Although not shown in the drawings, the pants-type diaper and its precursor may also be provided with a waist containment pocket and elasticised leg openings. Since such constructional features are however well known in the art, they will not be described in further detail.

The materials making up the pants-type diaper precursor 36 may be selected from any of the materials commonly used for such products and may include environmentally friendly materials from renewable sources and/or biodegradable material. Thus, the first web or topsheet 52 can include a nonwoven material, e.g. spunbond, meltblown, carded, hydroentangled, wetlaid, etc. Suitable nonwoven materials can be composed of man-made fibres, such as polyester, polyethylene, polypropylene, viscose, rayon, etc. or natural fibres, such as wood pulp or cotton fibres, or from a mixture of natural and man-made fibres. The topsheet material may further be composed of tow fibres, which may be bonded to each other in a bonding pattern, as e.g. disclosed in EP-A-1 035 818. Further examples of possible topsheet materials include porous foams, apertured plastic films, laminates of nonwoven materials and apertured nonwoven fabric, etc. The topsheet materials should be soft and non-irritating to the skin and be readily penetrated by body fluid, e.g. urine. The topsheet may further be different in different parts of the diaper.

The second web or backsheet 54 will form the outer cover of the completed pants-type diaper. The backsheet may be the same or different in different parts of the diaper. At least in the area of the absorbent structure 50, the backsheet includes a liquid impervious material in the form of a thin plastic film, e.g. a polyethylene or polypropylene film, a nonwoven material coated with a liquid impervious material, a hydrophobic nonwoven material, which resists liquid penetration, or a laminate of a plastic film and a nonwoven material. The backsheet material may be breathable so as to allow vapour to escape from the absorbent core, while still preventing liquids from passing there through. Examples of breathable backsheet materials are porous polymeric films, nonwoven laminates of spunbond and meltblown layers and laminates of porous polymeric films and nonwoven materials. The backsheet may include a nonwoven material on at least the undergarment-facing surface thereof.

The absorbent structure 50 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as superabsorbent materials can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are, in particular embodiments, lightly cross-linked to render the material substantially water insoluble. Particular superabsorbent materials can be surface cross-linked so that the outer surface or shell of the superabsorbent particle, fibre, flake, sphere, etc. possesses a higher crosslink density than the inner portion of the superabsorbent. The superabsorbent materials may be in any form which is suitable for use in absorbent composites including particles, fibres, flakes, spheres, and the like.

For reasons of improved fit and comfort, the first and second side panel portions 24, 26, 28, 30 may exhibit elastic properties at least in the transverse direction. The first and second side panel portions may include various suitable materials. In one embodiment, the material is an elastic web material in the form of an elastic laminate including a first layer of fibrous material and an elastic film layer. The elastic laminate may optionally include a second layer of fibrous material, with the elastic film layer being located between the first and second layers of fibrous material. However, it is to be understood that other types of elastic web materials may be used, such as elastic nonwoven materials, nonwoven materials which per se are inelastic, but which have been elastified by suitable means, etc. The elastic web materials may include one layer or two or more layers that have been laminated. The first and second layers of fibrous material may be chosen so that they, in combination with the inner elastic film layer, give the material high resistance to puncture. They also provide a soft and cloth-like feel to the laminate. Examples of suitable materials are carded webs and spunbond materials. The basis weight of the fibrous material layers should be between 10 and 35 g/m², preferably between 12 and 30 g/m², more preferably between 15 and 25 g/m². Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and in this way, give the nonwoven material a higher elongation at maximum load. A mixture of polyethylene and polypropylene polymers has proved to provide good results in this respect. A mixture of fibers of different polymers is also possible. The elastic film layer may be constituted by an apertured elastic film having a basis weight between 20 and 80 g/m², preferably between 20 and 60 g/m². The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

For reasons of comfort, it is advantageous if the total basis weight of the laminate can be kept low. Thus, although a total basis weight of about 150 g/m² is acceptable, a total basis weight of 100 g/m² or less, for example no more than 90 g/m², is preferred.

Such an elastic laminate may be manufactured according to the method disclosed in WO 03/047488, wherein one spunbond layer is applied to the film in a tacky state and will thus bond to the film layer, while the other spunbond layer is adhesively laminated to the film layer using for example a pressure sensitive hot melt adhesive.

The method disclosed in WO 03/047488 involves stretching of the laminate above the point of failure of the fibrous material, so that the non-elastic layers break completely. Therefore, as described in WO 03/047488, the elongation of the laminate is not limited by the stretch modulus of the non-elastic material.

To provide additional wearer comfort, the elastic laminate may be breathable and have a Water Vapour Transmission Rate according to ASTM E96-00 of at least 1500 g/m²-24 h, preferably at least 3000 g/m²-24 h.

Examples of elastic laminates are described in EP-B-0 646 062, WO 98/29251, WO 03/000165 and U.S. Pat. No. 5,226, 992. Examples of commercially available elastic laminates are Fabriflex™ 306 from Tredegar and PK 6358 from Nordenia.

As used herein, an elastic material is defined as a material having a permanent elongation after relaxation of less than 10% after the material has been subjected to an elongation of 30% in the elasticity test outlined below. An elongation of 30% means an elongation to a length that is 30% longer than the initial length of the sample. An inelastic material has a permanent elongation after relaxation of more than 10% after having been subjected to an elongation of 30%.

Elasticity Test

The method measures the behaviour of an elastic material at repeated load and unload cycles. The sample is stretched to a predetermined elongation and a cyclic movement between 0 and said predetermined elongation is performed. Desired load and unload forces are recorded. The permanent, i.e. remaining, elongation of the relaxed material is measured.

The permanent elongation after relaxation should be less than 10% and is measured by the method below. Thus an elastic elongation of 30% is defined as that the laminate should have a permanent relaxation after elongation of less than 10% after being exerted to an elongation of 30% in the tensile tester below. An elongation of 30% means an elongation to a length that is 30% longer than the initial length of the sample.

A tensile tester, e.g. Lloyd LRX™, able to perform cyclic movements and equipped with a printer/plotter or software presentation is used. The sample is prepared by cutting it to a width of 25 mm. The length and width of the sample may vary according to the available amount of material.

If the material to be tested has a width higher than 25 mm the sample should be cut so that the width is 25 mm. If however the material to be tested, e.g. the elastic material, has a width that is smaller than 25 mm the sample should have the width of the available material piece. The forces then have to be adjusted to the width of the sample according to the values given in brackets in the test method.

The tensile tester is calibrated according to the apparatus instructions. The parameters needed for the test (load and unload forces) are adjusted to:
  Crosshead speed: 500 mm/min
  Clamp distance: adapted to the length of the test sample
  Preload: 0.05 N (0.02 N/10 mm width)

The sample is placed in the clamps and it is made sure that the sample is centred and fastened perpendicularly in the clamps. Depending on the length of the sample the distance between the clamps may vary. If a sample is longer than 100 mm it should be cut to a length of 100 mm. A suitable distance between the clamps is in this case 50 mm. For shorter samples the distance between the clamps can be shorter then 50 mm but as long as possible. For very short samples, less than 20 mm, the elastic sample should at both ends still be attached to inelastic material of the belt member or side panels, wherein the inelastic material is fastened in the clamps with the elastic part of the sample extending between the clamps. It is in this case important that the entire elastic part of such a sample is located between the clamps.

The tensile tester is started and two cycles between 0 and the predetermined elongation are performed. The crosshead should return immediately and not be held in the stretched position. There should not be any delay between the two cycles of the test method. After the last cycle, the sample is relaxed for 1 minute, then the permanent elongation is measured by stretching the sample until a force of 0.1 N (0.04 N/10 mm width) is detected and the elongation is read.

How the precursor 36 illustrated in FIG. 2 is processed to form a completed pants-type diaper 10 will be explained in the following, initially with reference to FIG. 3.

Figure 3:
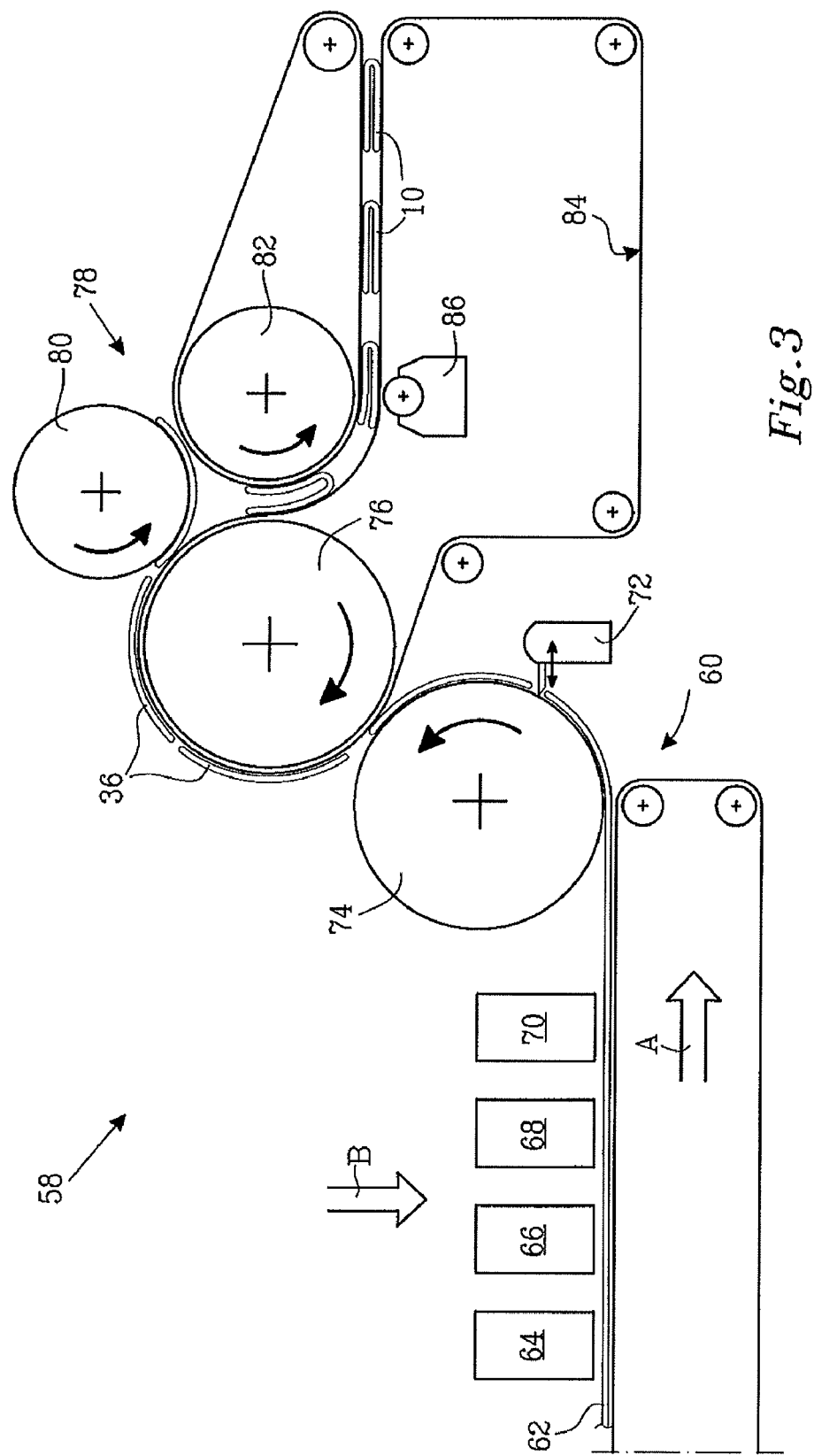
FIG. 3 is a schematic elevation view of apparatus for carrying out the method of an embodiment of the present invention.

In FIG. 3, reference number 58 generally denotes processing apparatus for converting pants-type diaper precursors 36 into completed pants-type diapers 10. The processing apparatus includes a first conveyor arrangement 60 for advancing a flat continuous web 62 in the machine direction A, the web having a predetermined width W in the cross-machine direction. In the present context, the term "flat" means that the continuous web is laid out in the cross-machine direction without any gatherings and under substantially no tension in the cross-machine direction. In the illustrated embodiments, the continuous web will ultimately form the backsheet or second web 54 of the diaper precursors. However, it is to be understood that the method of the invention is equally applicable to embodiments in which the flat continuous web 62 will constitute the topsheet 52 of a completed pants-type diaper. The continuous web 62 passes a number of stations at which components making up the diaper precursors are secured to the continuous web. These stations are illustrated purely schematically in FIG. 3 and may include a first station 64 at which the absorbent structures 50 are secured to the continuous web, a second station 66 at which the first and second side panel portions 24, 26, 28, 30 are secured to the continuous web, a third station 68 at which the waistband elastic 56 is secured to the continuous web and a fourth station 70 at which the topsheet or first web 52 is secured to the continuous web. Downstream of the first to fourth stations is a cutting station 72 at which the continuous web 62, together with the components which have been added at the preceding stations, is severed to form individual pants-type diaper precursors 36.

It is to be understood that the sequence in which the stations 64, 66, 68, 70 are arranged will be dependent on manufacturing techniques. For example, it is conceivable that the station at which the first and second side panel portions are secured to the continuous web precede the station at which the waistband elastic is secured. Similarly, the skilled person will appreciate that the absorbent cores may be secured to the continuous web subsequent to the securing of the side panels portions and/or the waistband elastic.

Downstream of the cutting station 72 the first conveying apparatus 60 further includes a first transfer drum 74 and a second transfer drum 76. The transfer drums are equipped with means to maintain the diaper precursors in a flat condition so that the backsheet 54 of each pants-type diaper precursor 36 maintains the same predetermined width W as the continuous web 62. These means may be constituted by suction and/or (not shown) mechanical clamping means which hold the first and second side edge regions 46, 48 of the pants-type diaper precursors in place against the transfer drums.

A folding unit, generally denoted by reference number 78, is provided to effect folding of the pants-type diaper precursors 36 about the transverse axis T or an axis parallel to the transverse axis T. In the apparatus shown in FIG. 3, the folding unit 78 includes a topsheet-engaging roller 80 and a backsheet-engaging roller 82, with the two rollers being arranged to rotate in the same direction. The backsheet-engaging roller 82 cooperates with a second conveyor arrangement 84 to transport folded-over pant-type diaper precursors to a seam-forming station 86 at which the seams 32, 34 are formed along edge margins of the first and second side panel portions 24, 26, 28, 30 of the diaper precursors. The seam forming station 86 may be constituted by any conventional seam-forming equipment, such as ultrasonic or resistive heating equipment. In one embodiment, the seam-forming equipment is constituted by rotary ultrasonic welding equipment.

The thus completed pants-type diapers 10 may then be transported to (not shown) further stations where, for example, the diapers are packaged for shipment.

Figure 4:
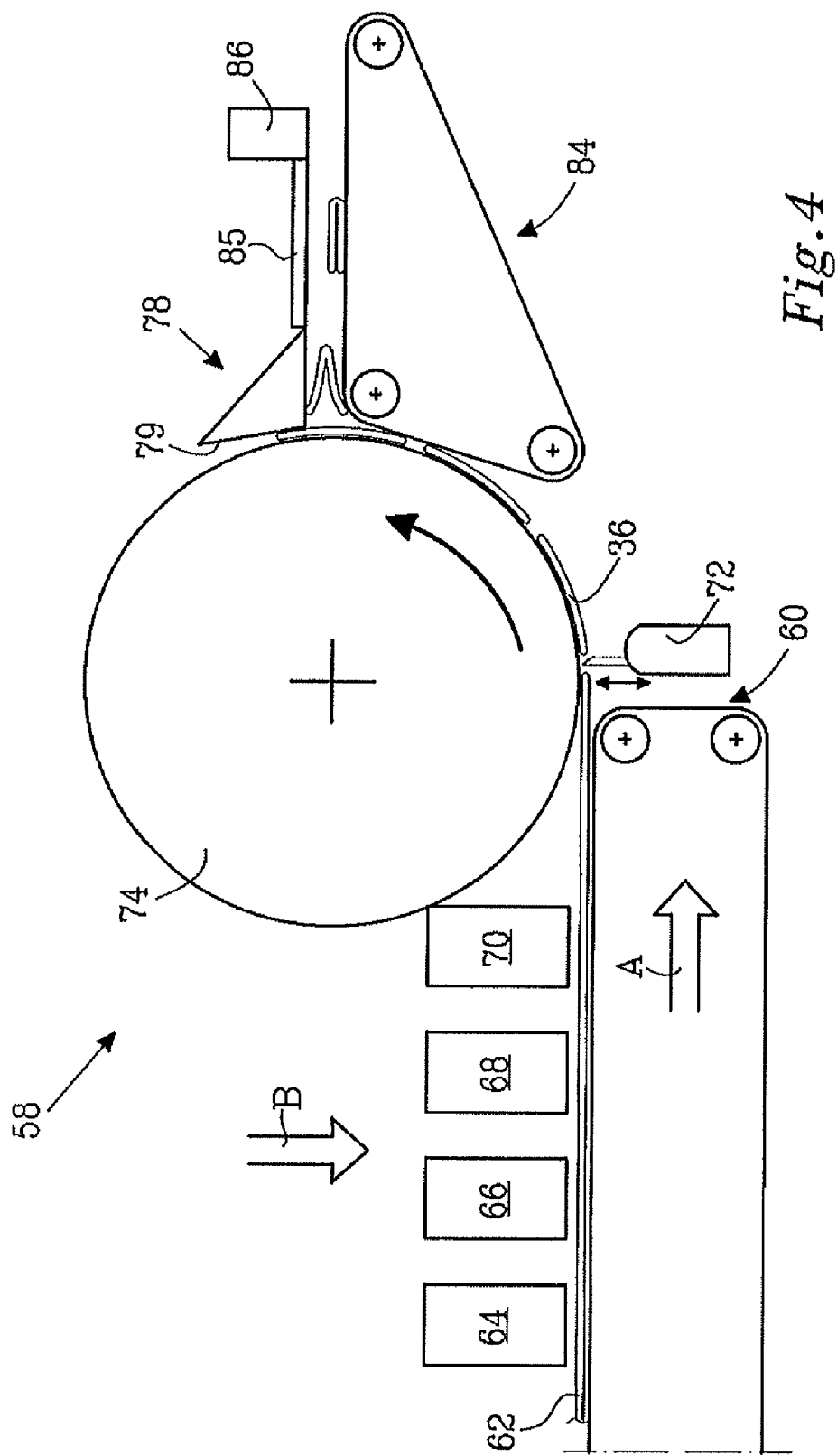
FIG. 4 is a schematic elevation view of further apparatus for carrying out the method of an embodiment of the present invention.

Other suitable processing apparatus is illustrated in FIG. 4 in which the same reference numbers are used for components corresponding to those of the processing apparatus FIG. 3. As with the FIG. 3 apparatus, the processing apparatus 58 of FIG. 4 includes a first conveyor arrangement 60 for advancing a flat continuous web 62 in the machine direction A, the web having a predetermined width W in the cross-machine direction. The continuous web 62 passes a number of stations at which components making up the diaper precursors are secured to the continuous web. Again, these stations may include a first station 64 at which the absorbent structures 50 are secured to the continuous web, a second station 66 at which the first and second side panel portions 24, 26, 28, 30 are secured to the continuous web, a third station 68 at which the waistband elastic 56 is secured to the continuous web and a fourth station 70 at which the topsheet or first web 52 is secured to the continuous web. As with the FIG. 3 apparatus, the actual order, or indeed presence, of all the various stations is insignificant for the present invention.

Downstream of the first to fourth stations there is a cutting station 72 at which the continuous web 62, together with the components which have been added at the preceding stations, is severed to form individual pants-type diaper precursors 36.

Downstream of the cutting station 72 the first conveying apparatus 60 further includes a first transfer drum 74. The transfer drum is equipped with means to maintain the diaper precursors in a flat condition so that the backsheet 54 of each pants-type diaper precursor 36 maintains the same predetermined width W as the continuous web 62. These means may be constituted by suction and/or (not shown) mechanical clamping means which hold the first and second side edge regions 46, 48 of the pants-type diaper precursors in place against the transfer drums.

A folding unit, generally denoted by reference number 78, is provided to effect folding of the pants-type diaper precursors 36 about the transverse axis T or an axis parallel to the transverse axis T. In the apparatus shown in FIG. 4, the folding unit 78 includes a strike plate 79 against which the leading edge region 40 of each pants-type diaper precursor is arranged to impact. As will be explained in greater detail below, the folding unit 78 cooperates with a second conveyor arrangement 84 to cause the first and second side panel portions 24, 28; 26, 30 along each side edge region 46, 48 of the diaper precursors 36 to be brought into overlapping relationship. An air blower assembly, schematically depicted at 85, can be used to blow air onto the overlapping side panel portions of the precursor to assist in the alignment of the side panel portions until the precursors 36 arrive at a seam forming station 86. The equipment at the seam forming station corresponds to the equipment mentioned above in relation to the FIG. 3 apparatus.

In order to carry out the method of embodiments of the present invention, the processing apparatus 58 is arranged to operate in the following manner.

The continuous web 62 of predetermined width W in the cross-machine direction is temporarily secured to the first conveyor arrangement 60 whilst substantially maintaining the predetermined width of the continuous web. Constituent components of the pants-type diaper precursors are then affixed to the continuous web at the various stations 64, 66, 68, 70. In the method of embodiments of the invention, these include securing the side panel portions 24, 26; 28, 30 to the continuous web, for example at the second station 66 and securing the elastic elements making up the waistband elastic 56 to the continuous web, for example at the third station 68. The elastic elements are secured under tension in the cross-machine direction to selected regions of the continuous web whilst substantially maintaining the predetermined width W of the continuous web. As is schematically illustrated in FIGS. 5A and 5B, these selected regions correspond at least to the trailing edge region 44 of the pants-type diaper precursor.

The thus equipped continuous web is severed at the cutting station 72 along cutting lines indicated by the dashed lines 1 in FIGS. 5A and 5B. This is performed whilst substantially maintaining the predetermined width W of the continuous web 62 to thereby form a plurality of the pants-type diaper precursors 36.

In the processing apparatus illustrated in FIG. 3, the individual pants-type diaper precursors are advanced by the first transfer drum 74 and the second transfer drum 76 towards the folding unit 78. At the folding unit the leading edge region 40 of the diaper precursor is released from the second transfer drum 76 of the first conveyor arrangement 60, for example by interrupting the vacuum source within the drum at that location, whilst the trailing edge region 44 remains secured to the drum 76. The topsheet-engaging roller 80 of the folding unit picks up the leading edge region 40 and transports it towards the backsheet-engaging roller 82. Since the trailing edge region is still secured to the second transfer drum 76, when the leading edge region 40 engages the backsheet-engaging roller 82 the diaper precursor will tend to be folded about its transverse axis T such that the first and second side panel portions 24, 26; 28, 30 are brought into overlapping relationship. The pants-type diaper precursors 36 are then transferred to the second conveyor arrangement 84 at which the trailing edge region 44 is temporarily secured to the second conveyor arrangement. Seams 32, 34 are then formed along edge margins of the first and second side panel portions at the seam-forming station 86 to thereby form a pants-type diaper 10.

Similarly, in the processing apparatus in FIG. 4, the individual pants-type diaper precursors 36 are advanced by the first transfer drum 74 towards the folding unit 78. At the folding unit the leading edge region 40 of the diaper precursor is released from the first transfer drum 74 of the first conveyor arrangement 60, for example by interrupting the vacuum source within the drum at that location, whilst the trailing edge region 44 remains secured to the drum 74. The leading edge region 40 impacts the strike plate 79 and the trailing edge region 44 is released from the first conveyor arrangement and transferred to the second conveyor arrangement 84. The diaper precursor will tend to be folded about its transverse axis T such that the first and second side panel portions 24, 26; 28, 30 are brought into overlapping relationship. The pants-type diaper precursors 36 are then transported along the second conveyor arrangement 84 to the seam-forming station 86 at which seams 32, 34 are formed along edge margins of the first and second side panel portions to thereby form a pants-type diaper 10.

In accordance with embodiments of the invention, the step of securing elastic elements 56 under tension in the cross-machine direction to selected regions of the continuous web 62 whilst substantially maintaining the predetermined width W of the continuous web is carried out so as to provide a pants-type diaper 10 in which a force difference is present between the force necessary to cause the trailing edge region 44 to attain the predetermined width W and the force necessary to cause the leading edge region 40 to attain the predetermined width, with the force for the trailing edge region being greater than the force for the leading edge region.

As previously explained, since the leading edge region 40 of the pants-type diaper precursor is released from the conveyor arrangement for a relatively long period of time to permit folding of the diaper precursor about its transverse axis panel whilst the trailing edge region 44 is retained on the conveyor arrangements for substantially all of this period, the fact that a force difference is present between the force necessary to cause the trailing edge region 44 to attain the predetermined width W and the force necessary to cause the leading edge region 40 to attain the predetermined width, with the force for the trailing edge region being greater than the force for the leading edge region, means that the degree of contraction or necking of the leading edge region and the trailing edge region when they are unsupported by the conveyor arrangement will be essentially the same, even though the leading edge region is unsupported for a much longer period than the trailing edge region. As such, the first and second side panel regions will tend to arrive at the seam-forming station in correct overlapping relationship for forming the seams.

The actual value of force difference to ensure correct overlapping relationship will, to a large extent, be dependent on the production speed of the processing apparatus. For typical production speeds, for example up to 400 units/min, the force difference is between 1.0 N and 5.0 N, preferably between 1.5 N and 4.0 N, more preferably between 2.0 N and 4.0 N.

Non-limiting ways in which the above-described force difference can be attained will be explained in the following with reference to FIGS. 5A and 5B.

In FIG. 5A, a single strip of waistband elastic 56 is secured to the continuous web 62 at a location at which the waistband elastic overlaps the cutting line 1. The strip is secured in a tensioned condition such that its length is about 90% greater than its non-tensioned length. Thus, for a non-tensioned strip length of 60 mm, the strip of waistband elastic will have a tensioned length of 114 mm. The location is chosen such that a wider section of the waistband elastic is provided in the trailing edge region 44 of a downstream diaper precursor than in the leading edge region 40 of an adjacent upstream diaper precursor. Once the continuous web is severed along the cutting lines 1, each diaper precursor will have a waistband elastic in the trailing edge region 44 which exerts a greater contracting force than the waistband elastic in the leading edge region 40. This in turn means that the force necessary to cause the trailing edge region 40 of a thus provided pants-type diaper 10 to attain the predetermined width W of the continuous web will be greater than the equivalent force in the leading edge region. By suitable selection of the relative widths of the waistband elastic in the leading and trailing edge regions, a desired force difference can be obtained.

In FIG. 5B, separate elastic elements serve as the waistband elastic in the leading and trailing edge regions. As illustrated in FIG. 5B, the desired force difference is attained by using a narrower strip of waistband elastic in the leading edge region 40 compared with the trailing edge region. In a not shown alternative, the desired force difference may be achieved by securing the waistband elastic in the trailing edge region under greater tension than that in the leading edge region. A further manner of achieving the desired force difference is to provide waistband elastic in the trailing edge region only. A still further conceivable manner is to use different waistband elastic material in the leading and trailing edge regions.

Since the waistband elastic 56 is applied to the flat continuous web 62 with the elastic under tension, the predetermined width which is to be attained to ascertain whether the force in the trailing edge region is greater than the force in the leading edge region will correspond to the flat, i.e. non-gathered, condition of the backsheet of the pants-type diaper 10. The actual forces are measured in the following manner.

A first test sample is cut from the trailing edge region 44 along a first cut line parallel to the transverse axis T. A second test sample is cut from the leading edge region 40 along a second cut line parallel to the transverse axis T. Each test sample should include the entire waistband elastic 56 in its respective edge region. Normally, the waistband elastic will not be wider than 30 mm and so a sample width, i.e. the distance of the first cut line from the trailing edge 42 and the second cut line from the leading edge 38, of 40 mm is recommended. In the case that the waistband elastic extends over a length greater than 40 mm then the test sample shall include the entire waistband elastic. The thus cut out test sample is then placed in the jaws of a tensile tester, for example a Lloyd LRX™, with the waistband elastic centered with respect to the jaws. The actual material that is clamped by the jaws should exclude the waistband elastic. Instead, the clamped material should be the non-gathered backsheet and topsheet.

The tensile tester is calibrated according to the apparatus instructions. The parameters needed for the test (load and unload forces) are adjusted to:

Crosshead speed: 500 mm/min
Clamp distance: adapted to the length of the test sample
Preload: 0.08 N (0.02 N/10 mm width)

The tensile tester is started and the force at which the backsheet becomes non-gathered, i.e. reaches the flat condition of the continuous web 62, is determined. This force can easily be read from the resulting stress/strain curve and corresponds to the point on the curve at which the gradient increases sharply as the backsheet/topsheet material reaches its non-gathered length and starts to resist deformation. This force corresponds to the force necessary to cause the test sample to reach the predetermined width of the continuous web 62. By comparing the results for the first and second test samples, it can be determined whether the force necessary to cause the first test sample to attain the predetermined width is greater than the force necessary to cause the second test sample to attain the predetermined width. Similarly, by subtracting the force value for the second test sample form that for the first test sample, it can be ascertained whether the force differences described in this disclosure have been achieved. Clearly, if no waistband elastic is present in the leading edge region 40, the force difference will correspond to the value of force necessary to cause the first test sample to attain the predetermined width.

The invention has been described above by way of example only and the skilled person will appreciate that many changes can be made within the scope of the appended claims. For example, although the precursor 36 has been illustrated with the leading edge region 40 corresponding to at least a part of the front panel 12 of the completed diaper, it is to be understood that the method is equally applicable to a precursor in which the leading edge region corresponds to a part of the rear panel 14 of the completed diaper. The skilled person will further appreciate that suction is only one way in which the pants-type diaper precursor can be temporarily secured to the conveyor arrangements and that clamps, pressing plates and the like may be used additionally or instead.

The invention claimed is:

1. A method for facilitating an alignment of first and second side panel portions of a pants-type diaper whilst feeding a pants-type diaper precursor in a machine direction through a processing apparatus, said pants-type diaper precursor comprising a leading edge region, a trailing edge region and first and second side edge regions, each of said first and second side edge regions having said first side panel portion at said leading edge region and said second side panel portion at said trailing edge region, the method comprising the steps of:

providing a flat continuous web having a predetermined width in the cross-machine direction, the cross-machine direction being perpendicular to the machine direction;
temporarily securing said continuous web to a first conveyor arrangement of said processing apparatus whilst substantially maintaining said predetermined width of the continuous web;
securing said side panel portions to said continuous web;
securing elastic elements under tension in the cross-machine direction to selected regions of said continuous web whilst substantially maintaining said predetermined width of the continuous web, said selected regions corresponding at least to said trailing edge region of said pants-type diaper precursor;
severing said continuous web whilst substantially maintaining said predetermined width of the continuous web to thereby form a plurality of said pants-type diaper precursors;
advancing said pants-type diaper precursor towards a folding unit at which said leading edge region is released from said first conveyor arrangement;
bringing said first and second side panel portions into overlapping relationship;
transferring said pants-type diaper precursor to a second conveyor arrangement at which said trailing edge region is temporarily secured to said second conveyor arrangement, and
forming seams along edge margins of said first and second side panel portions to thereby form a pants-type diaper,
wherein said step of securing elastic elements under tension in the cross-machine direction to selected regions of said continuous web whilst substantially maintaining said predetermined width of the continuous web is carried out so as to provide a pants-type diaper in which a force difference is present between the force necessary to cause the trailing edge region to attain said predetermined width and the force necessary to cause the leading edge region to attain said predetermined width, with the force for the trailing edge region being greater than the force for the leading edge region.

2. The method as claimed in claim 1, wherein said force difference is between 1.0 N and 5.0 N.

3. The method as claimed in claim 1, wherein during the step of securing elastic elements under tension in the cross-machine direction to selected regions of said continuous web whilst substantially maintaining said predetermined width of the continuous web, said selected regions correspond solely to said trailing edge region of said pants-type diaper precursor.

4. The method as claimed in claim 1, wherein during the step of securing elastic elements under tension in the cross-machine direction to selected regions of said continuous web whilst substantially maintaining said predetermined width of the continuous web, said selected regions correspond to said trailing edge region and said leading edge region of said pants-type diaper precursor.

5. The method as claimed in claim 4, wherein a single elastic element applied under tension is applied to a selected region of said continuous web, said selected region corresponding to both said trailing edge region and said leading edge region of said pants-type diaper precursor.

6. The method as claimed in claim 5, wherein during the step of severing said continuous web said single elastic element is severed such that a greater portion of said elastic element is provided in said trailing edge region of a pants-type diaper precursor than in said leading edge region of an adjacent pants-type diaper precursor.

7. The method as claimed in claim 1, wherein the pants-type diaper precursor has an absorbent structure sandwiched between a first web and a second web, one of said first and second webs being constituted by a section of said continuous web, said first web being intended to be worn against a wearer's skin and said second web being intended to be worn against a wearer's clothing, wherein during the step of advancing said pants-type diaper precursor towards a folding unit, said first web faces said first conveyor arrangement immediately prior to folding.

8. The method as claimed in claim 7, wherein said first conveyor arrangement comprises at least one revolving drum.

9. The method as claimed in claim 7, wherein during the step of transferring said pants-type diaper precursor to a second conveyor arrangement at which said trailing edge region is temporarily secured to said second conveyor arrangement, said second web of said pants-type diaper precursor is caused to face the second conveyor arrangement.

10. The method as claimed in claim 1, wherein the pants-type diaper precursor has an absorbent structure sandwiched between a first web and a second web, one of said first and second webs being constituted by a section of said continuous web, said first web being intended to be worn against a wearer's skin and said second web being intended to be worn against a wearer's clothing, wherein during the step of advancing said pants-type diaper precursor towards a folding unit, said second web faces said first conveyor arrangement immediately prior to folding.

11. The method as claimed in claim 1, wherein said pants-type diaper precursor is temporarily secured to said first and second conveyor arrangements at least by suction.

12. The method as claimed in claim 1, wherein the step of forming seams along edge margins of said first and second side panel portions is performed using ultrasonic welding equipment.

13. The method as claimed in claim 1, wherein between the steps of bringing said first and second side panel portions into overlapping relationship, and forming seams along edge margins of said first and second side panel portions, the method further includes the step of causing air to be blown onto the first and second side panel portions to assist in maintaining alignment thereof.

14. The method as claimed in claim 1, wherein said elastic elements are constituted by a ribbon of elastomeric material.

15. The method as claimed in claim 14, wherein said elastic elements are constituted by a three-layered laminate of PP-SBS-PP, in which PP is polypropylene and SBS is styrene/butadiene/styrene.

16. The method of claim 14, wherein the elastomeric material is natural rubber, synthetic rubber, a thermoplastic elastomeric polymer, a stretch bonded laminate, a neck bonded laminate, or an elastic nonwoven.

* * * * *